(12) United States Patent  
Steinmueller

(10) Patent No.: US 8,899,753 B2  
(45) Date of Patent: *Dec. 2, 2014

(54) OPHTHALMOLOGICAL ANALYSIS INSTRUMENT AND METHOD

(75) Inventor: Andreas Steinmueller, Wettenberg (DE)

(73) Assignee: Oculus Optikgeraete GmbH (DE)

( * ) Notice: Subject to any disclaimer, the term of this patent is extended or adjusted under 35 U.S.C. 154(b) by 189 days.

This patent is subject to a terminal disclaimer.

(21) Appl. No.: 13/597,088

(22) Filed: Aug. 28, 2012

(65) Prior Publication Data

US 2013/0050648 A1    Feb. 28, 2013

(30) Foreign Application Priority Data

Aug. 30, 2011   (DE) .......................... 10 2011 081 827

(51) Int. Cl.
*A61B 3/10* (2006.01)
*A61B 3/107* (2006.01)
*A61B 3/11* (2006.01)

(52) U.S. Cl.
CPC ................. *A61B 3/107* (2013.01); *A61B 3/101* (2013.10); *A61B 3/11* (2013.01)
USPC .......................................... 351/221; 351/246

(58) Field of Classification Search
USPC .......... 351/206, 246, 221, 208, 212; 600/558, 600/398, 401, 405, 587; 356/498, 503
See application file for complete search history.

(56) References Cited

U.S. PATENT DOCUMENTS

| | | | |
|---|---|---|---|
| 5,349,398 A | 9/1994 | Koester | |
| 5,532,772 A | 7/1996 | Fujieda et al. | |
| 5,841,509 A | 11/1998 | Harooni et al. | |
| 5,975,700 A | 11/1999 | Koest | |
| 6,004,314 A | 12/1999 | Wei et al. | |
| 2007/0273830 A1 | 11/2007 | Levine | |
| 2008/0309872 A1 | 12/2008 | Hara et al. | |
| 2008/0316499 A1* | 12/2008 | Korb et al. | ..................... 356/503 |
| 2009/0046250 A1 | 2/2009 | Mattioli et al. | |

FOREIGN PATENT DOCUMENTS

| | | |
|---|---|---|
| CN | 1728965 A | 2/2006 |
| CN | 102961120 A | 3/2013 |
| DE | 69023007 T2 | 7/1996 |
| DE | 102004055683 A1 | 5/2006 |
| EP | 0697611 A2 | 2/1996 |
| EP | 1723900 A1 | 11/2006 |

(Continued)

OTHER PUBLICATIONS

European Patent Office, Search Report, EP 12180837.2, Dec. 13, 2012.

(Continued)

*Primary Examiner* — Hung Dang

(74) *Attorney, Agent, or Firm* — Quarles & Brady LLP

(57) ABSTRACT

An ophthalmological analysis instrument for measuring a topography of a surface of an eye includes a projection apparatus and a monitoring apparatus. The projection apparatus has at least one illumination device and an aperture device. The illumination device has a first light source. The aperture device images an image pattern on a surface of an eye. The monitoring apparatus has a camera and an objective lens, wherein images of the imaged image pattern being recordable by the monitoring apparatus, and a topography of the surface being derivable from the images. A magnification of the image can be varied by means of the objective lens.

17 Claims, 1 Drawing Sheet

(56) References Cited

FOREIGN PATENT DOCUMENTS

| | | |
|---|---|---|
| EP | 1857043 A2 | 11/2007 |
| EP | 2016888 A1 | 1/2009 |
| JP | S5975035 A | 4/1984 |
| JP | S62253028 A | 11/1987 |
| JP | S63125236 A | 5/1988 |
| JP | H01091829 A | 4/1989 |
| JP | H06285027 A | 10/1994 |
| JP | H09276224 A | 10/1997 |
| JP | H11513580 A | 11/1999 |
| JP | 2000516500 A | 12/2000 |
| JP | 2001238853 A | 9/2001 |
| JP | 2008086435 A | 4/2008 |
| JP | 2009066109 A | 4/2009 |
| JP | 2009285108 A | 12/2009 |
| JP | 2011156030 A | 8/2011 |
| KR | 100791749 B1 | 1/2008 |
| KR | 20100107014 A | 10/2010 |
| WO | 9714351 A1 | 4/1997 |
| WO | 9806320 A1 | 2/1998 |
| WO | 2007042854 A1 | 4/2007 |
| WO | 2011038457 A1 | 4/2011 |
| WO | 2011093209 A1 | 8/2011 |

OTHER PUBLICATIONS

European Patent Office, Search Report, EP 12180837.2, May 13, 2013.
Korean Intellectual Property Office, Notice of Rejection, Application No. 10-2012-0092833, Dec. 24, 2013, 6 pages.
Japan Patent Office, Notice for a Reason of Rejection (English Translation of the First Office Action in Japan), Patent Application No. 2012-187796, Sep. 13, 2013, 4 pages.
English Translation of the Japanese Patent Office Decision of Final Rejection, Patent Application No. 2012-187796, Apr. 4, 2014, 2 pages.
Korean Intellectual Property Office, Notice of Rejection, Application No. 10-2012-0092833, Jun. 23, 2014, 3 pages [English Language Translation Only].
The State Intellectual Property Office of P.R. China, First Office Action and Search Report, Application No. 201210316618.X, Mar. 28, 2014, 16 pages [English Language Translation Only].

* cited by examiner

OPHTHALMOLOGICAL ANALYSIS INSTRUMENT AND METHOD

CROSS REFERENCE TO RELATED APPLICATION

The present application claims the benefit of German Patent Application No. 10 2011 081 827.3 filed Aug. 30, 2011, which is fully incorporated herein by reference.

STATEMENT REGARDING FEDERALLY SPONSORED RESEARCH OR DEVELOPMENT

Not applicable.

FIELD OF THE INVENTION

The invention relates to an ophthalmological analysis instrument and to an analysis method, in particular for measuring a topography of a surface of an eye, said analysis instrument having a projection apparatus and a monitoring apparatus, the projection apparatus comprising at least one illumination device and an aperture device, the illumination device having at least one first light source, it being possible to image an image pattern on a surface of an eye by means of the aperture device, the monitoring apparatus having a camera and an objective lens, images of the imaged image pattern being recordable by means of the monitoring apparatus, and a topography of the surface being derivable from the images.

BACKGROUND OF THE INVENTION

In the analysis instruments and topography systems known from the prior art, an eye is generally illuminated with monochromatic light, such as infrared light for example, so as to avoid dazzling the person or subject to be examined where possible. Topography systems are thus known which, in addition to measuring a surface of an eye, also enable pupillometric measurements. In particular when the eye is illuminated with monochromatic light, which is only partly visible, a contraction of the pupil is effectively prevented, and therefore an illumination of this type is particularly well suited for pupillometric measurements. Topography systems may, however, also have a plurality of light colours for illumination of an eye. For example, Placido rings are then projected onto the eye in different monochromatic light colours. This is basically used for distinction of the rings of the image pattern imaged on the eye and for the sole purpose of determining a topography. Placido rings of this type in different monochromatic light colours consequently form the first light source alone. It is further known to examine meibomian glands under infrared light.

Analysis instruments for measuring topography or what are known as "keratometers" can also be used for non-invasive analysis of a tear film on an eye. The image pattern projected onto the surface of the eye is recorded substantially continuously, wherein any break-up in the tear film can be identified by a change to the image pattern. In order to establish the quality of the tear film, a break-up time thereof is generally measured. This measurement is likewise carried out by illuminating the eye with infrared light. For example, in addition to the topography of the surface of the eye, a measurement of a tear film is also of utmost importance when selecting contact lenses. Furthermore, analysis of a tear film is limited merely to a distribution of the tear film over the eye. A disadvantage of the known analysis instrument and method is that the possibilities for examining an eye are limited. It is therefore desirable to broaden the examination possibilities of an instrument of this type so as to obtain further and more detailed measurement results where necessary, which can be used for example for improved contact lens selection and fitting.

The object of the present invention is therefore to propose an ophthalmological analysis instrument and an analysis method which uses an ophthalmological analysis instrument, with which the examination possibilities of a topography system are broadened and improved.

This object is achieved in one embodiment of the invention by an apparatus having a projection apparatus including at least one illumination device and an aperture device, the illumination device having at least one first light source, the aperture device being capable of imaging an image pattern on a surface of an eye; and a monitoring apparatus having a camera and an objective lens said monitoring apparatus being capable of recording images of the imaged image pattern, wherein a topography of the surface of the eye being derivable from the images, and a magnification of the images can be varied by the objective lens. This object is also achieved in a second embodiment of the invention by a method including the steps of imaging an image pattern onto the surface of the eye using the aperture device; recording images of the imaged image pattern using the monitoring apparatus; and deriving a tear film flow from the images by measuring a speed of movement of particles situated on the surface of the eye.

The ophthalmological analysis instrument according to the invention, in particular for measuring a topography of a surface of an eye, has a projection apparatus and a monitoring apparatus, the projection apparatus comprising at least one illumination device and an aperture device, the illumination device having at least one first light source, it being possible to image an image pattern on a surface of an eye by means of the aperture device, the monitoring apparatus having a camera and an objective lens, images of the imaged image pattern being recordable by means of the monitoring apparatus, and a topography of the surface being derivable from the images, wherein a magnification of the image can be varied by means of the objective lens.

Since the monitoring apparatus has a camera and an objective lens, the images obtained are quality images which can be utilised effectively. It is thus possible, depending on the type of measurement, to select a magnification of the objective lens in such a way that the object to be measured or the property to be measured can be visually illustrated such that evaluation of the image and particularly accurate measurement results are generally made possible. In particular in the case of a very large magnification, it is possible to focus the tear film such that particles situated in the tear film are visible, for example dust particles or foreign bodies. Any movement of these particles can be tracked and measured with respect to direction of movement and speed. The direction in which and the speed at which the tear film flows can be derived from this. This measurement can be used to determine tear film quality more accurately.

To this end, the objective lens may have a magnification changer, by means of which at least one lens can be introduced into a beam path of the objective lens and removed therefrom. Compared to a variable magnification adjustment, which is likewise conceivable, a magnification changer can be produced particularly easily and cost effectively. It is also possible to always use constant, standardised magnifications for the various measurements, which simplifies considerably the measurements and an evaluation or analysis of the images.

At least three magnifications can advantageously be formed by means of the objective lens. A first, normal magnification can be used to measure the topography of the surface of the eye. A second, large magnification can be used to measure or analyse a tear film. For example, it is possible to focus on a lipid layer, in particular with shallow depth of field, so as to determine the thickness of said lipid layer. A third, small magnification can be used in particular for meibometric examination, since the recording of images of meibomian glands requires an enlarged spacing between the analysis instrument and the eye inter alia.

The first light source may also emit light in a predominantly monochromatic spectrum. The light of the first light source can thus be better identified by the monitoring apparatus.

The first light source may advantageously emit light in a predominantly infrared spectrum. Infrared light has a particularly low dazzling effect on the eye to be examined and is easily produced.

The illumination device may have at least one further light source, which can emit polychromatic light in a predominantly visible spectrum. In addition to the use of substantially monochromatic light or light of a relatively narrow wavelength range, the further light source may make it possible to illuminate the surface of the eye with polychromatic, visible light, whereby additional measurements of properties of the eye and attainment of more accurate measurement results are possible. Compared to monochromatic or infrared light, it is possible to determine a degree of reddening of the eye using polychromatic light. It is also possible to measure a thickness of a tear film or of a lipid layer of the tear film relatively accurately in a non-invasive manner, since coloured interference patterns of the lipid layer can be produced using polychromatic light and can be used for measurements of this type.

It is particularly advantageous if the further light source can emit predominantly white light. Particularly good colour reproduction can be achieved with white light, which considerably improves measurement accuracy, in particular when measuring the degree of reddening of the eye and when producing a coloured interference pattern.

In one embodiment, the further light source can be formed from a multiplicity of uniformly distributed light-emitting diodes. For example, the light-emitting diodes themselves may form the image pattern. The light-emitting diodes can thus be arranged in a ring or behind an aperture, which can project the image pattern onto the eye. The light-emitting diodes which form the further light source can be arranged on the illumination device together with light-emitting diodes which form the first light source. It is thus possible to operate the relevant light-emitting diodes separately or together, as required. A number of light-emitting diodes of the first light source to a number of light-emitting diodes of the further light source can be selected in a ratio of 1 to 3.

It is particularly advantageous if, for a beam path of the monitoring apparatus, an opening is formed in the aperture device in an instrument axis of the aperture device orientable in the direction of an optical axis of the eye. The surface of the eye can thus be illuminated on all sides with the image pattern by means of the aperture device. For example, the aperture device can thus be formed from an illuminating ring or a plurality of concentric rings of this type so as to produce a Placido image pattern. If the instrument axis of the aperture device is oriented toward the optical axis of the eye, the beam path of the monitoring apparatus can extend directly along the optical axis or thereover, so that the eye can be monitored from the front through the opening, thus considerably simplifying pupillometric measurements in particular.

The analysis instrument may thus also have a dazzling apparatus for exciting a dazzling stimulus onto the eye, the dazzling apparatus possibly having a dazzling light source and a beam splitter for reflecting the dazzling light source into the beam path of the monitoring apparatus. The eye can thus be dazzled by this dazzling apparatus, wherein a response of the eye can be recorded at the same time by means of the monitoring apparatus. For example, a movement of the pupil prompted by the dazzling can be recorded and evaluated. The dazzling apparatus can be operated independently of the illumination device and image patterns produced thereby.

It is further possible to utilise the illumination device and/or the dazzling apparatus for dazzling the eye with the objective of increasing production of tear fluid. The formation of a tear film can thus be examined and measured.

The analysis method according to the invention is carried out using an ophthalmological analysis instrument for measuring a topography of a surface of an eye, the analysis instrument comprising a projection apparatus and a monitoring apparatus, the projection apparatus comprising at least one illumination device and an aperture device, an image pattern being imaged onto the surface of the eye by means of the aperture device, images of the imaged image pattern being recorded by means of the monitoring device, a tear film flow being derived from the images, and a speed of movement of particles situated on the surface being measured.

In particular with very large magnification, it is possible to focus the tear film such that particles situated in the tear film are visible, for example dust particles or foreign bodies. Any movement of these particles is tracked and measured with respect to direction of movement and speed. The direction in which and the speed at which the tear film flows can be derived from this. This measurement is used to determine tear film quality more accurately.

In one embodiment of the method, the analysis instrument may have an evaluation apparatus, by means of which the images are analysed. The evaluation apparatus may advantageously be arranged in the analysis instrument itself and can enable processing of the images and a visualised output of the measurement results established by the evaluation apparatus. In particular, the evaluation apparatus may comprise data processing means, which can also carry out digital processing of the images. It is also conceivable for the data processing means to have a data store with a database, wherein the database may have comparative data sets of images or measurement parameters. For example, simplified conclusions regarding probable measurement results or corrections of measurement results can be drawn from comparative data sets of this type, for example as a result of image comparison. Evaluation can be accelerated considerably and measurement accuracy can be increased further.

The illumination device may also have at least one light source which emits polychromatic light in a predominantly visible spectrum, wherein a tear film on the surface can be determined from the images. A particularly accurate examination of the tear film is made possible in particular by the use of polychromatic, visible light to illuminate the eye and the tear film with the image pattern.

Furthermore, a degree of reddening of the eye can be determined from the images, a proportion of red in a region of the eye being measurable. A measurement of this type cannot be carried out using infrared light or monochromatic light due to the lack of colour reproduction. During the measurement process, a reddening of the region surrounding the iris of the eye can thus be measured by quantification of the red image portions due to the good colour reproduction of the polychromatic, visible light. The measurement can be carried out as a comparative measurement, for example by comparison with a reference image.

A tear film break-up time can also be derived from the images, wherein a change to the tear film can be measured. A tear film break-up time can be measured with normal magnification, and the measurement can be carried out under illumination with infrared light or visible light. The image patterns projected onto the surface of the eye, such as Placido rings, make it possible to identify any break-up of the tear film, in particular as a result of a change to the image pattern in question. A break-up time of a tear film can be considered to be a basic parameter for determining quality of the tear film.

Furthermore, a lipid layer on the tear film can be determined from the images, wherein the lipid layer can be measured by interference colours. A lipid layer is an outer layer of the tear film, wherein a central, aqueous layer and an inner layer adjacent to the cornea (mucin layer) follow after the lipid layer. The lipid layer is approximately 100 nm thick, prevents rapid evaporation of the aqueous layer and is formed from a secretion of the meibomian glands. Since the lipid layer is a very thin layer of the tear film, it can be measured very easily using interference colours. The eye or the tear film can thus be illuminated with polychromatic light, whereby the thickness of the interference colours or an interference pattern can be produced on the tear film by means of the aforementioned lipid layer. Possible tear film properties can thus be determined more accurately.

It is thus possible to determine a lipid layer thickness or thickness distribution of the lipid layer as well as the thickness thereof and also to examine the function of the meibomian glands on the basis of the measurable amount of lipids. A large magnification may preferably be selected for a measurement of this type.

Further advantageous embodiments of the method will emerge from the description of features of the claims.

BRIEF DESCRIPTION OF THE DRAWINGS

A preferred embodiment of the invention will be explained in greater detail hereinafter with reference to the accompanying drawings, in which.

DETAILED DESCRIPTION OF THE EXAMPLE EMBODIMENTS

Figure 1:
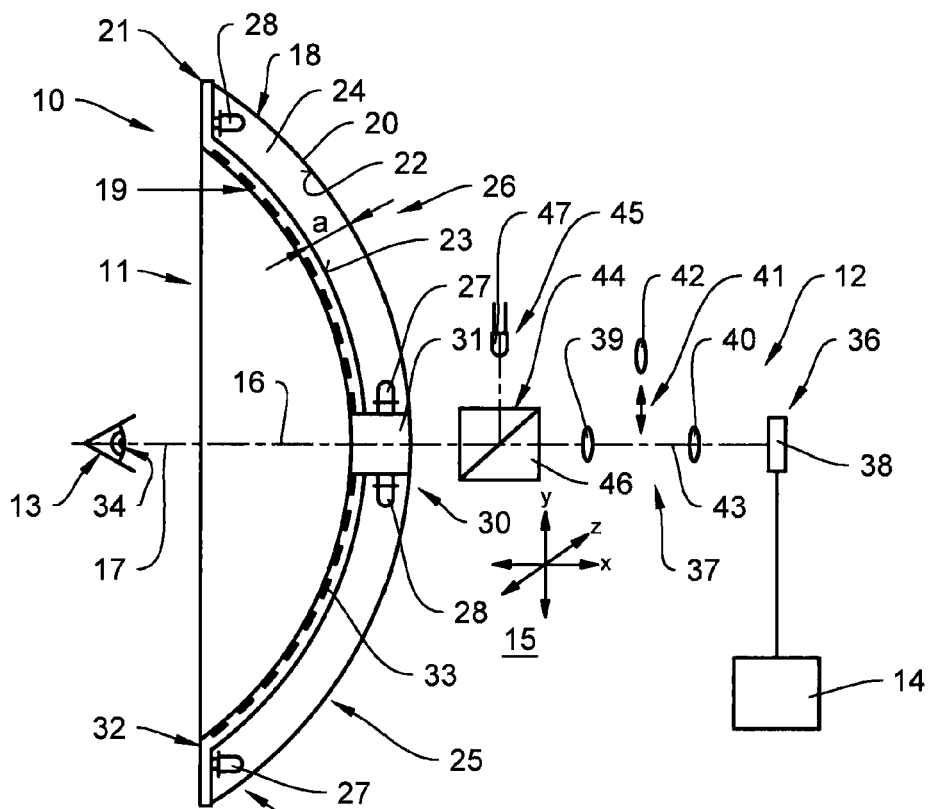
FIG. 1 shows a simplified, schematic sectional view of an embodiment of an analysis instrument.
Figure 2:
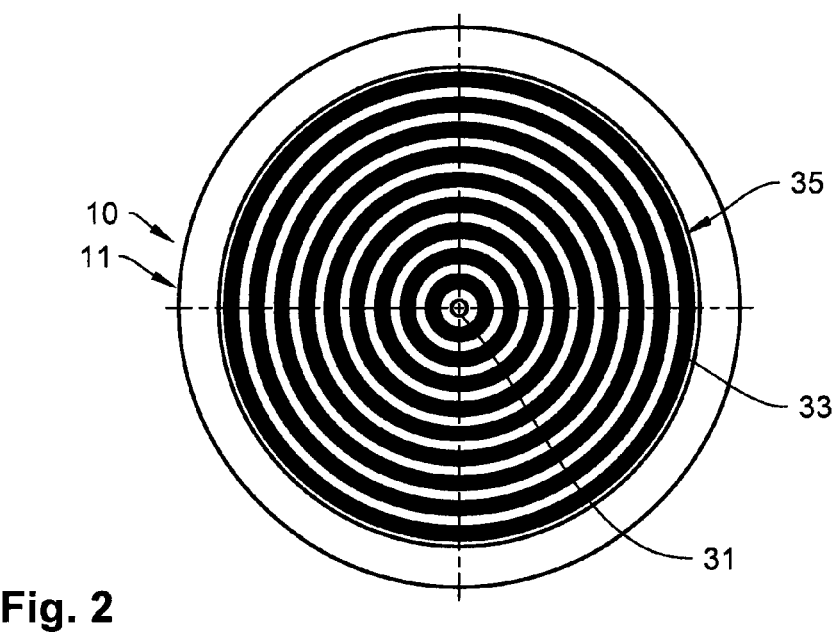
FIG. 2 shows a front view of the analysis instrument.

An overview of FIGS. 1 and 2 shows an embodiment of an analysis instrument 10, which is formed basically from a projection apparatus 11 and a monitoring apparatus 12 for monitoring an eye 13. The analysis instrument 10 further comprises an evaluation apparatus 14, in this case with means (not illustrated in greater detail) for data processing and for data output as well as a positioning apparatus 15 for positioning the analysis instrument 10 relative to the eye 13 in three spatial directions having the direction components x, y and z arranged at right angles to one another, as indicated symbolically in this case. The analysis instrument is positioned in such a way that an instrument axis 16 of the analysis instrument 10 coincides with an optical axis 17 of the eye 13.

The projection apparatus 11 is formed as a hollow spherical segment 18 and comprises a screen aperture 19 and a reflector 20, which are fixed in a housing 21 (indicated schematically) in such a way that a reflecting area 22 of the reflector 20 is always spaced from a surface 23 of the reflector 20 at the same distance a, thus forming a curved aperture space 24. The surface 23 of the reflector 20 is highly reflective, and therefore the aperture space 24 is filled uniformly with light when a first light source 25 or a further light source 26 is switched on. The light sources 25 and 26 are each formed from light-emitting diodes 27 and 28, which are each arranged in a uniformly distributed multiplicity in the manner of a ring 29 over a circumference of the screen aperture 19 and in the manner of a ring 30 at an opening 31 in the screen aperture 19. The screen aperture 19 is basically formed from a transparent body 32 having annular aperture elements 33, which reflect incident light from a light source 25 and/or 26 into the aperture space 24. The image pattern 35 visible in FIG. 2 is thus imaged onto a cornea 34 of the eye 13, wherein the image pattern 35 is recorded by means of the monitoring apparatus 12.

The monitoring apparatus 12 has a camera 36 with an objective lens 37, wherein the camera 36 comprises an optical video sensor 38 inter alia, which is connected directly to the evaluation apparatus 14. The objective lens 37 is formed from two lenses 39 and 40, wherein a magnification changer 41 is provided (as indicated in this case by the double-headed arrow), by means of which further lenses 42 can be pivoted into a beam path 43 of the monitoring apparatus 12. It is thus possible to record and observe the eye 13 in at least three different magnifications. A beam splitter 44 of a dazzling apparatus 45 is arranged in the beam path 43 between the projection apparatus 11 and the objective lens 37, and consists of a prism system 46, but can also be formed from partially transparent, flat mirrors. A dazzling light source 47 can be imaged in the eye 13 via the beam splitter 44. A dazzling stimulus can thus be excited on the eye 13, completely independently of the projection apparatus 11, and therefore the response of said eye can be recorded with the aid of the monitoring apparatus 12, which is available in any case, and can also be determined numerically by the evaluation apparatus 14. A special instrument is accordingly no longer necessary for such a measurement.

With regard to the functioning of the analysis instrument 10, the light-emitting diodes 27 can emit or irradiate light in a predominantly infrared spectrum and the light-emitting diodes 28 can emit or irradiate polychromatic, white light in a predominantly visible spectrum. The first light source 25 is formed by approximately 50 light-emitting diodes 27, and the further light source 26 is formed by approximately 150 light-emitting diodes 28. Within a measurement process, the first light source 25 or the further light source 26 can be switched on, as required, to illuminate the eye 13. In particular to determine a topography of the eye 13, it is sufficient to use the first light source 25 with normal magnification of the objective lens 37. The first light source 25 is also used for meibometric examinations, wherein a small magnification of the objective lens 37 is selected in this instance and a spacing between the analysis instrument 10 and the eye 13 is enlarged. The further light source 26 is used for analysis of a tear film, in particular of a lipid layer of the tear film, wherein a particularly large magnification of the objective lens 37 is selected. In addition, the dazzling light source 47 is used for pupillometric measurements.

The invention claimed is:

1. An ophthalmological analysis instrument for measuring a topography of a surface of an eye, said analysis instrument comprising:
a projection apparatus including at least one illumination device and an aperture device, the illumination device having at least one first light source, the aperture device being capable of imaging an image pattern on a surface of an eye; and a monitoring apparatus having a camera and an objective lens, said monitoring apparatus being capable of recording images of the imaged image pattern, wherein a topography of the surface of the eye being derivable from the images, and a magnification of the images can be varied by the objective lens.

2. The analysis instrument according to claim 1, in which the objective lens has a magnification changer, wherein at least one lens can be introduced into a beam path of the objective lens and removed therefrom via the magnification changer.

3. The analysis instrument according to claim 1, in which at least three magnifications can be formed.

4. The analysis instrument according to claim 1, in which the first light source can emit light in a predominantly monochromatic spectrum.

5. The analysis instrument according to claim 4, in which the first light source can emit light in a predominantly infrared spectrum.

6. The analysis instrument according to claim 1, in which the illumination device has at least one further light source, which can emit polychromatic light in a predominantly visible spectrum.

7. The analysis instrument according to claim 6, in which the further light source can emit predominantly white light.

8. The analysis instrument according to claim 6, in which, the further light source is formed from a multiplicity of uniformly distributed light-emitting diodes.

9. The analysis instrument according to claim 1, in which for a beam path of the monitoring apparatus, an opening is formed in the aperture device in an instrument axis of the aperture device orientable in the direction of an optical axis of the eye.

10. The analysis instrument according to claim 9, in which the analysis instrument includes a dazzling apparatus for exciting a dazzling stimulus onto the eye, the dazzling apparatus having a dazzling light source and a beam splitter reflecting the dazzling light source into the beam path of the monitoring apparatus.

11. An analysis method using an ophthalmological analysis instrument for measuring a topography of a surface of an eye, said analysis instrument having a projection apparatus and a monitoring apparatus, the projection apparatus comprising at least one illumination device and an aperture device, said method comprising:

imaging an image pattern onto the surface of the eye using the aperture device;

recording images of the imaged image pattern using the monitoring apparatus; and deriving a tear film flow from the images by measuring a speed of movement of particles situated on the surface of the eye.

12. The analysis method according to claim 11, including analyzing the images using an evaluation apparatus forming part of the analysis instrument has an evaluation apparatus, by means of which the images are analyzed.

13. The analysis method according to claim 11, including determining a tear film on the surface of the eye from the images, wherein the surface of the eye is illuminated by the illumination device having at least one light source, which emits polychromatic light in a predominantly visible spectrum.

14. The analysis method according to claim 13, including measuring a proportion of red in a region of the eye to determine a degree of reddening of the eye from the images.

15. The analysis method according to claim 11, including deriving a tear film break-up time from the images by measuring a change to the tear film.

16. The analysis method according to claim 11, including determining a lipid layer on the tear film from the images using interference colors.

17. The analysis method according to claim 16, including measuring a lipid layer thickness.

* * * * *